United States Patent [19]

Evans et al.

[11] 4,216,168

[45] Aug. 5, 1980

[54] PREPARATION OF HIGH PURITY TETRAHYDROCARBYLAMMONIUM TETRAHYDRIDOBORATES

[75] Inventors: Francis E. Evans, Hamburg; Charles J. Lind, Gowanda; Martin A. Robinson, East Amherst, all of N.Y.

[73] Assignee: Allied Chemical Corporation, Morris Township, Morris County, N.J.

[21] Appl. No.: 951,822

[22] Filed: Oct. 16, 1978

Related U.S. Application Data

[63] Continuation-in-part of Ser. No. 855,145, Nov. 28, 1977, abandoned.

[51] Int. Cl.² ............................................. C07C 85/00
[52] U.S. Cl. ............................................. 260/567.6 M
[58] Field of Search ................................. 260/567.6 M

[56] References Cited

U.S. PATENT DOCUMENTS

| | | | |
|---|---|---|---|
| 2,738,369 | 3/1956 | Banus et al. | 260/567.6 M |
| 2,928,719 | 3/1960 | Perner et al. | 23/14 |
| 2,942,935 | 6/1960 | King et al. | 23/14 |
| 3,108,139 | 10/1963 | Larchar | 260/567.6 |
| 3,506,828 | 4/1970 | Hansen et al. | 260/567.6 M |

OTHER PUBLICATIONS

Banus et al., "J.A.C.S.", vol. 74 (1952), pp. 2346–2348.
King et al., "J.A.C.S.", vol. 78 (1956), p. 4176.
Titov et al., "Chem. Abstracts", vol. 72 (1970), 110687y.

*Primary Examiner*—Joseph E. Evans
*Attorney, Agent, or Firm*—Jay P. Friedenson

[57] ABSTRACT

High purity tetrahydrocarbylammonium tetrahydridoborates are prepared under anhydrous conditions by reacting tetrahydrocarbylammonium salts with at least 8% molar excess of an alkali metal hydroxide in the presence of ethanol to produce the corresponding tetrahydrocarbylammonium hydroxides and alkali metal salts, removing the alkali metal salts and adding an alkali metal borohydride to the solution to produce the corresponding tetrahydrocarbylammonium tetrahydridoborates and alkali metal hydroxides.

13 Claims, No Drawings

PREPARATION OF HIGH PURITY TETRAHYDROCARBYLAMMONIUM TETRAHYDRIDOBORATES

CROSS REFERENCE TO RELATED APPLICATION

This application is a continuation-in-part of U.S. application Ser. No. 855,145, filed Nov. 28, 1977 now abandoned.

FIELD OF THE INVENTION

This invention relates to a novel and improved method for the preparation of high purity tetrahydrocarbylammonium tetrahydridoborates.

BACKGROUND OF THE INVENTION

It is known to prepare tetrahydrocarbylammonium tetrahydridoborates by reaction of tetrahydrocarbylammonium salts with an alkali metal borohydride, however, by such process yields are low and the product is contaminated with the alkali metal salt by-products.

In order to improve yields and product quality, it has been proposed to react a tetrahydrocarbylammonium hydroxide with an alkali metal borohydride in an aqueous solution followed by drying the reaction mixture and extracting the dry solid mix of products with ethyl alcohol to remove the alkali metal hydroxide formed. Better yields are obtained with this approach but many process steps have been added and the possibility for hydrolysis of the borohydride radical exists.

Other known methods for the preparation of this class of products involve the use of more expensive materials such as $LiAlH_4$ or $MgB_2$ or the use of more complicated and thus, costly process methods.

It is an object of this invention to provide a simple economic process for the preparation of tetrahydrocarbylammonium tetrahydridoborates in high purity or good yields, with good product quality and with a minimum of processing steps.

The tetrahydrocarbylammonium tetrahydridiborates are a known class of compounds and are known to be useful in a wide variety of chemical reactions as reducing agents such as for aldehydes and ketones to the corresponding acids and aldehydes, reduction of acid chlorides to the corresponding alcohols, reduction of primary and secondary amides to the corresponding amines, reduction of organic disulfides to the corresponding mercaptans, and reduction of anhydrides. Generally, these materials may be used for the same general class of reactions as known to be useful for the well known alkali metal borohydrides including in addition to the above-mentioned reduction reactions, the halogenation under solvolytic conditions of secondary and tertiary alkyl halides which are capable of forming stable carbonium ions to the corresponding hydrocarbons, demercuriation reactions, and a variety of other organic and inorganic reactions. For some applications a high purity product is required or desired.

SUMMARY OF THE INVENTION

It has been found that the object of the invention may be achieved by carrying out the following steps under anhydrous conditions: (a) reacting a tetrahydrocarbylammonium salt with at least an 8% molar excess of an alkali metal hydroxide in the presence of ethanol to produce the corresponding tetrahydrocarbylammonium hydroxide and alkali metal salt, (b) removing the alkali metal salt and (c) adding an alkali metal borohydride to the solution to produce the corresponding tetrahydrocarbylammonium tetrahydridoborate and alkali metal hydroxide.

DETAILED DESCRIPTION OF THE INVENTION AND OF THE PREFERRED EMBODIMENTS

The novel process of the invention may be used to prepare tetrahydrocarbylammonium high purity tetrahydridoborates of the formula $$R_1R_2R_3R_4NBH_4$$

wherein $R_1$, $R_2$, $R_3$ and $R_4$ may be independently selected from the group consisting of alkyl containing 1–6 carbon atoms. $R_1$ and $R_2$ may be straight chain or branched chain radicals such as methyl, n-hexyl, t-butyl, and isopropyl. The preferred carbon content for the $R_1$ and $R_2$ groups is 1–2 carbon atoms and most preferably 1 or methyl.

By high purity is intended to mean 97.5% pure or higher. It is essential, in order to achieve a high purity product, that all process steps be crried out under andhydrous conditions. The presence of water, even in relatively small amounts has been found to deleteriously affect the purity of the desired products. In order to achieve the desired anhydrous environment for the process of the invention, anhydrous (i.e. <1000 ppm $H_2O$ and, preferably <400 ppm $H_2O$) reactants and ethanol solvent should be employed and all equipment should be dried before use such as by purging with an inert gas such as nitrogen. Further, a dry atmosphere should be maintained during all process operations such as by maintaining an inert gas atmosphere, and the final product should be stored under anhydrous conditions, such as under a dry inert gas. Use of a dry inert gas atmosphere during the process operations affords the further advantage of preventing formation of color bodies.

According to the invention process, after establishing the required anhydrous atmosphere, a tetrahydrocarbylammonium salt starting material of the formula $$R_1R_2R_3R_4N^+X^-$$

wherein $R_1$, $R_2$, $R_3$ and $R_4$ are as defined above and $X^-$ is an anion from an inorganic salt, is reacted with at least an 8% excess of an alkali metal hydroxide of the formula $$MOH$$

wherein M is an alkali metal, in the presence of ethanol as solvent for both reactants. The alkali metal hydroxide and ethanol reagents are anhydrous or dried appropriately before use.

The alkali metal M may be any of the alkali metals from Group IA of the Periodic Table such as Na, K, Li, Rb and Cs, but is preferably Na or K, most preferably Na.

The anion for the starting material is not critical. Any anion which reacts with the alkali metal of the alkali metal hydroxide is suitable. Illustrative suitable anions include the halides such as the chlorides, bromides and iodides and the sulfates. Preferably, the anion should be one which forms an insoluble salt with the alkali metal hydroxide in order to facilitate separation of the salt from the reaction mixture. Generally the chlorides, sulfates and bromides form sufficiently insoluble salts to satisfy this objective. The iodides as a class generally form more soluble salts and would tend to remain in solution, however, these salts, as is the case with other soluble salts, may generally be extracted from the solution by ordinary chemical means.

Although a variety of inert organic solvents may be employed which will permit the reactions of interest to proceed; it is essential, in order to obtain high purity product of the type described herein, to use ethanol as the solvent.

In the above-described reaction, the tetrahydrocarbylammonium salt starting material reacts with the alkali metal hydroxide in ethanol to produce a solution of the corresponding tetrahydrocarbylammonium hydroxide in ethanol and a salt formed by the alkali metal hydroxide reactant with the anion of the starting material salt.

The reaction may be conveniently carried out at room temperature; however the reaction temperature is not critical. Generally, elevated temperatures from about 30° C. up to the boiling point of the reaction mixture promote the reaction. The preferred temperature range is from 50° C.–80° C.

The molar ratio of the alkali metal hydroxide to the starting material reactant is critical to obtain a high purity product as described herein. At least an 8% molar excess of the alkali metal hydroxide must be employed. Preferably, at least a 10% molar excess of the alkali metal hydroxide is employed and still preferably, at least a 20% excess is employed. When molar excesses of alkali metal hydroxide of at least 8% but below about 15% are employed, extra vigorous extraction of the salts from the final product, such as by multiple reslurrying in alcohol, may be required to achieve the desired product purity. Molar excesses of the alkali metal hydroxide greater than about 33% will not deleteriously affect the reaction but offer no economic advantage.

The tetrahydrocarbylammonium hydroxide product of the above reaction is in solution with the ethanol solvent with precipitated alkali metal salt or dissolved alkali metal salt depending upon its solubility. At this point the salt is removed by ordinary physical means, such as by filtration or extraction. This reduces the possibility of contamination of the final product with the salt as would be the case if the salt were removed from the final product.

Following the removal of the salt, the ethanol solution of the tetrahydrocarbylammonium hydroxide having the formula

$R_1R_2R_3R_4N^+OH^-$ wherein $R_1$, $R_2$, $R_3$ and $R_4$ are as defined above, is then reacted with an alkali metal borohydride of the formula

$M_1BH_4$ wherein $M_1$ is an alkali metal as described for M in the MOH reactant discussed above. Here again, K and Na are preferred, most preferably Na.

The alkali metal borohydride reacts with the tetrahydrocarbylammonium hydroxide to produce a solution of the corresponding tetrahydrocarbylammonium tetrahydridoborate and by-product alkali metal hydroxide in ethanol.

Temperatures for the above reaction are not critical. The reaction may be carried out at room temperatures, however, generally elevated temperatures from about 30° C. up to the boiling point of the reaction mixture promote the reaction. The preferred temperature range is from 50° C.–80° C.

The molar ratio of the tetrahydrocarbylammonium hydroxide to the alkali metal borohydride should be at least stoichiometric, that is to at least 1:1 and preferably should be in excess to insure complete reaction. An excess of the tetrahydrocarbylammonium hydroxide will not deleteriously affect the reaction but a substantial excess will complicate purification.

The tetrahydrocarbylammonium tetrahydridoborate final product is a solid and may be recovered by ordinary filtration procedures and impurities may be removed by standard extraction procedures with organic solvents.

EXAMPLE 1

Preparation of Tetramethylammonium Tetrahydridoborate 164.4 Grams of 97 weight % tetramethylammonium chloride (equal to 159.47 grams or 1.456 moles of 100% product) were dissolved in 500 grams of anhydrous 2 B alcohol (anhydrous ethanol containing up to 2 weight % benzene) by heating to about 60°–65° C. with agitation. 80 Grams of 97 minimum wt. % NaOH (equal to 77.6 grams or 1.94 moles of 100% product or a 33% molar excess based on the tetramethylammonium chloride) were dissolved in 690 grams of anhydrous 2 B alcohol by heating to about 65°–70° C. with agitation. The hot sodium hydroxide solution was added to the hot solution of tetramethylammonium chloride over a period of about 15 minutes with agitation. A precipitate of NaCl was formed. The reaction product was then digested at about 60°–70° C. for a period of 1 hour and then cooled to 0°–10° C. over a period of about 2 hours. The resulting mixture was then filtered cold and the filtered solid washed with cold anhydrous 2 B alcohol. The filtrate and washes were then combined for the next reaction sequence. 53 Grams of 98 weight % minimum sodium borohydride (equal to 51.94 grams or 1.373 moles of 100% product) were added to the solution of tetramethylammonium hydroxide obtained in the first reaction sequence over a period of 15 minutes at 20°–30° C. with vigorous stirring. A precipitate of tetramethylammonium tetrahydridoborate rapidly formed. Agitation was continued for 30 minutes at 20°–30° C. and then the temperature of the reaction mixture was increased to 50°–60° C. and the reaction mass digested for a period of 1 hour. The reaction mass was then cooled to 10°–15° C. over a period of 1–2 hours and filtered. The filter cake was washed with several portions of anhydrous 2 B alcohol and then reslurried in anhydrous 2 B alcohol in order to reduce traces of contamination by chloride and sodium. The yield of tetramethylammonium tetrahydridiborate was 85% and the product assays over 98.5% activity and contains less then 0.1% chloride ion and less than 0.2% sodium ion.

EXAMPLE 2

Preparation of Tetramethylammonium Tetrahydridoborate

This example demonstrates the criticality of employing anhydrous conditions to obtain high purity product according to the invention process.

The process of Example 1 was repeated except that 95% ethanol (5 weight % water) was substituted for the anhydrous ethanol of Example 1. The yield of tetramethylammonium tetrahydridoborate was 92.9% but the purity was less than 90% (unacceptable).

EXAMPLES 3–6

These examples demonstrate the criticality of employing at least a minimum excess of the alkali metal hydroxide according to the invention process.

EXAMPLE 3

The process of Example 1 is repeated except that 0.2 mole tetramethylammonium chloride was dissolved in 69 grams of anhydrous 2 B alcohol, 0.21 mole of NaOH (corresponding to a 5% molar excess) was dissolved in 75 grams of anhydrous 2 B alcohol and 0.189 mole of sodium borohydride was added to the solution of tetramethylammonium hydroxide. The purity of the tetramethylammonium tetrahydridoborate product was 89.7% (unacceptable).

EXAMPLE 4

The process of Example 1 is repeated except that 1.57 moles (62.8 grams as 100% product) of NaOH (corresponding to an 8% molar excess) are dissolved in 545 grams of anhydrous 2 B alcohol. The purity of the tetramethylammonium tetrahydridoborate product is over 97.5%.

EXAMPLE 5

The process of Example 1 is repeated except that 1.595 moles (63.8 grams as 100% product) of NaOH (corresponding to a 10% molar excess) are dissolved in 550 grams of anhydrous 2 B alcohol. The purity of the tetramethylammonium tetrahydridoborate product is over 97.5%.

EXAMPLE 6

The process of Example 1 was repeated except that 8 moles (877 grams as 100% product) tetramethylammonium chloride were dissolved in 2500 grams of anhydrous 2 B alcohol, 9.75 moles (390 grams as 100% product) of NaOH (coresponding to a 22% molar excess) were dissolved in 2800 grams of anhydrous 2 B alcohol and 7.96 moles (301 grams as 100% product) of sodium borohydride were added to the solution of tetramethylammonium hydroxide. The purity of the tetramethylammonium tetrahydridoborate product was 98.6%.

EXAMPLES 7–15

The process of Example 1 is repeated excepting that the reactants and products are varied as indicated in the following Table. Similar results are obtained and that is to say good yields of the products in high purity are obtained.

TABLE

| Example | Tetrahydrocarbylammonium Salt | Alkali Metal Hydroxide | Alkali Metal Borohydride | Tetrahydrocarbylammonium Tetrahydridoborate |
|---|---|---|---|---|
| 7 | di-n-hexyl, dimethyl ammonium iodide | NaOH | NaBH$_4$ | di-n-hexyl, dimethyl ammonium tetrahydridoborate |
| 8 | trimethyl, isopropyl ammonium sulfate | KOH | KBH$_4$ | trimethyl, isopropyl ammonium tetrahydridoborate |
| 9 | trimethyl, cetyl ammonium bromide | LiOH | LiBH$_4$ | trimethyl, cetyl ammonium tetrahydridoborate |
| 10 | trimethyl, cyclopentyl ammonium chloride | RbOH | RbBH$_4$ | trimethyl, cyclopentyl ammonium tetrahydridoborate |
| 11 | dimethyl, ethyl, vinyl ammonium chloride | CsOH | CsBH$_4$ | dimethyl, ethyl, vinyl ammonium tetrahydridoborate |
| 12 | triethyl, 3,4-cyclopentenyl ammonium sulfate | NaOH | NaBH$_4$ | trialkyl, 3,4-cyclopentenyl ammonium tetrahydridoborate |
| 13 | trimethyl, phenyl ammonium iodide | NaOH | NaBH$_4$ | trimethyl, phenyl ammonium tetrahydridoborate |
| 14 | methyl, ethyl, xylyl ammonium chloride | KOH | KBH$_4$ | methyl, ethyl, xylyl ammonium tetrahydridoborate |
| 15 | trimethyl, naphthyl ammonium chloride | LiOH | LiBH$_4$ | trimethyl, naphthyl ammonium tetrahydridoborate |

We claim:

1. The process for preparing high purity tetrahydrocarbylammonium tetrahydridoborates of the formula $$R_1R_2R_3R_4NBH_4$$

wherein $R_1$, $R_2$, $R_3$ and $R_4$ may be independently selected from the group consisting of alkyl containing 1–6 carbon atoms, which comprises carrying out the following steps under anhydrous conditions and at temperatures from about 30° C. up to the boiling point of the reaction mixture:

(a) reacting a tetrahydrocarbylammonium salt starting material of the formula $$R_1R_2R_3R_4N^+X^-$$

wherein $R_1$, $R_2$, $R_3$ and $R_4$ are as defined above and wherein $X^-$ is an anion from an inorganic salt, with at least 8% molar excess of an alkali metal hydroxide of the formula $$MOH$$

wherein M is an alkali metal, in the presence of anhydrous ethanol to produce a tetrahydrocarbylammonium hydroxide of the formula $$R_1R_2R_3R_4N^+OH^-$$

wherein $R_1$, $R_2$, $R_3$ and $R_4$ are as defined above in solution with the ethanol, and the corresponding alkali metal salt, (b) removing the alkali metal salt, and (c) reacting the $R_1R_2R_3R_4N^+OH^-$ organic solvent solution with an alkali metal borohydride of the formula $$M_1BH_4$$

wherein $M_1$ is an alkali metal.

2. The process according to claim 1 in which at least a 10% molar excess of the alkali metal hydroxide is employed.

3. The process according to claim 1 in which at least a 20% molar excess of the alkali metal hydroxide is employed.

4. The process according to claim 1 in which $X^-$ is selected from the group consisting of halides and sulfates.

5. The process according to claim 1 in which $X^-$ is a halide.

6. The process according to claim 1 in which $R_1$, $R_2$, $R_3$ and $R_4$ are each methyl groups.

7. The process according to claim 1 in which $X^-$ is selected from a chloride and a bromide.

8. The process according to claim 5 in which $R_1$, $R_2$, $R_3$ and $R_4$ are each methyl groups.

9. The process according to claim 8 in which M and $M_1$ are each Na.

10. The process according to claim 9 in which $X^-$ is chloride.

11. The process according to claim 10 in which at least a 10% molar excess of the alkali metal hydroxide is employed.

12. The process according to claim 11 in which at least a 20% molar excess of the alkali metal hydroxide is employed.

13. The process according to claim 12 in which the process is carried out under an inert gas atmosphere.

* * * * *